: US008955162B2

(12) United States Patent
Huh

(10) Patent No.: US 8,955,162 B2
(45) Date of Patent: Feb. 17, 2015

(54) WELDING HELMET INCLUDING ANTI-BLINDING DEVICE TO SELECTIVELY AND CONVENIENTLY CONTROL WELDING OPERATION AND GRINDING OPERATION

(75) Inventor: Moon Young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 162 days.

(21) Appl. No.: 12/729,615

(22) Filed: Mar. 23, 2010

(65) Prior Publication Data

US 2011/0010815 A1    Jan. 20, 2011

(30) Foreign Application Priority Data

Jul. 15, 2009   (KR) .................. 10-2009-0064277
Feb. 26, 2010   (KR) .................. 10-2010-0018018

(51) Int. Cl.
*A61F 9/06* (2006.01)
(52) U.S. Cl.
CPC .................................... *A61F 9/067* (2013.01)
USPC ................................................... 2/8.8; 2/8.2
(58) Field of Classification Search
USPC ........ 2/7, 8.1, 8.2, 8.3, 8.4, 8.7, 8.8, 6.2, 422, 2/9, 905, 906
See application file for complete search history.

(56) References Cited

U.S. PATENT DOCUMENTS

| | | | | |
|---|---|---|---|---|
| 4,498,202 A * | 2/1985 | Yamamoto | ........................ | 2/424 |
| 4,546,498 A * | 10/1985 | Fantin | ........................ | 2/424 |
| 4,679,255 A * | 7/1987 | Kuhlman | ........................ | 2/8.3 |
| 4,863,244 A * | 9/1989 | Fuerthbauer et al. | ........... | 349/14 |
| 4,945,572 A * | 8/1990 | Rosen | ........................ | 2/8.3 |
| 5,315,099 A * | 5/1994 | Gunz et al. | .................. | 250/201.1 |
| 5,327,588 A * | 7/1994 | Garneau | ........................ | 2/422 |
| 5,510,961 A * | 4/1996 | Peng | ........................ | 362/106 |
| D393,933 S * | 4/1998 | Huh | ........................ | D29/110 |
| 5,751,258 A * | 5/1998 | Fergason et al. | .................. | 345/7 |
| 5,896,579 A * | 4/1999 | Johnson et al. | ..................... | 2/8.6 |
| 6,008,466 A * | 12/1999 | Hosoda | .................. | 219/121.62 |
| 6,070,264 A * | 6/2000 | Hamilton et al. | .................. | 2/8.8 |
| 6,115,846 A * | 9/2000 | Truesdale | .................. | 2/209.13 |
| D446,887 S * | 8/2001 | Young | ........................ | D29/107 |
| 6,483,090 B1 | 11/2002 | Bae | | |
| 6,552,316 B1 | 4/2003 | Bae | | |
| 6,614,409 B1* | 9/2003 | Bae | ........................ | 345/8 |
| D481,832 S * | 11/2003 | Huh | ........................ | D29/110 |
| D482,503 S * | 11/2003 | Huh | ........................ | D29/110 |
| 6,760,925 B1* | 7/2004 | Maxwell | ........................ | 2/171.3 |
| 6,973,672 B2* | 12/2005 | Huh | ........................ | 2/8.1 |

(Continued)

FOREIGN PATENT DOCUMENTS

KR   10-0679896   2/2007

*Primary Examiner* — Andrew W Collins
(74) *Attorney, Agent, or Firm* — Cantor Colburn LLP

(57) ABSTRACT

Disclosed is a welding helmet including an anti-blinding device to selectively control a welding operation and a grinding operation, and more particularly, a welding helmet, which stably protects the welder's eyes and enables easy switching of the anti-blinding device from a welding operation mode to a grinding operation mode or vice versa without taking off the welding helmet. In addition to the anti-blinding device to protect the welder's eyes from light emitted from a welding or cutting torch during a welding or grinding operation, a switch is provided at an outer surface of the welding helmet to allow a welder to conveniently select a welding operation mode or a grinding operation mode without taking off the welding helmet.

1 Claim, 12 Drawing Sheets

(56) References Cited

U.S. PATENT DOCUMENTS

| | | | |
|---|---|---|---|
| 7,462,806 B2 * | 12/2008 | Huh | 250/205 |
| 7,470,880 B2 | 12/2008 | Huh | |
| 7,564,014 B2 | 7/2009 | Huh | |
| 7,802,318 B2 * | 9/2010 | Chen | 2/171.3 |
| 7,926,118 B2 * | 4/2011 | Becker et al. | 2/8.2 |
| 2007/0056073 A1 * | 3/2007 | Martin et al. | 2/8.8 |
| 2007/0079417 A1 * | 4/2007 | Huh | 2/8.2 |
| 2008/0120752 A1 * | 5/2008 | Huh | 2/8.1 |

* cited by examiner

WELDING HELMET INCLUDING ANTI-BLINDING DEVICE TO SELECTIVELY AND CONVENIENTLY CONTROL WELDING OPERATION AND GRINDING OPERATION

BACKGROUND OF THE INVENTION

1. Field of the Invention

The present invention relates to a welding helmet including an anti-blinding device to selectively control a welding operation and a grinding operation, and more particularly, to a welding helmet, which stably protects the welder's eyes and enables easy switching of an anti-blinding device from a welding operation mode to a grinding operation mode or vice versa without taking off the welding helmet (i.e. a protective mask).

2. Description of the Related Art

Generally, during a welding, cutting, or grinding operation, a welding helmet is used to protect the welder's eyes from glare and various toxic substances. Recently, a variety of kinds of safe and convenient electronic welding helmets have been developed and used. FIG. 1 is a perspective view illustrating a conventional electronic welding helmet including an anti-blinding device. As illustrated in FIG. 1, the conventional electronic welding helmet 1 includes a welding light detection anti-blinding device 2 worn on the welder's head to control exposure to light emitted from a welding or cutting torch.

The welding helmet 1, which is provided at a front surface thereof with the anti-blinding device 2, may reduce the illumination intensity of light directed to the welder's eyes using an anti-blinding plate 5. The anti-blinding plate 5 takes the form of a Liquid Crystal Display (LCD) included in the anti-blinding device 2.

Specifically, the anti-blinding device 2 further includes a photo sensor 4, such as, e.g., a photodiode attached to a front surface thereof. The photo sensor 4 is adapted to sense light emitted from a welding or cutting torch. As a control circuit mounted in the anti-blinding device 2 controls the anti-blinding plate 5 to be darkened such that the illumination intensity of light passing through the anti-blinding plate 5 is reduced, the anti-blinding device 2 may serve to protect the eyes of the welder who wears the welding helmet 1.

The above described conventional electronic welding helmet including the anti-blinding device has been developed to provide the welder with a fixed darkness degree of a liquid crystal shutter, or to change a darkness degree of the shutter to a standard level according to a welding operation environment. The conventional electronic welding helmet also enables not only control of a shutter operation to shield welding light, but also variable control of a shutter delay time to prevent blinding of the welder's eyes by light emitted from a base metal after welding. In addition, a variety of control switches or variable volume switches required for the shutter operation are provided at specific positions of the electronic welding helmet to maximize convenience of use by the welder.

However, in the case of the conventional welding light detection anti-blinding device, it is necessary for the welder to manually control On/Off of power, darkness adjustment of the liquid crystal shutter, sensitivity adjustment of the photo sensor, and the control switches or the variable volume switches for time delay. This may cause inconvenience in a welding operation.

FIG. 2 is a block diagram illustrating an electromagnetic wave detection anti-blinding device as disclosed in Korean Patent No. 0679896 that was filed and registered by the applicant of the present invention to solve the above described problems. FIG. 3 is a view illustrating a conventional electromagnetic wave detecting unit, and FIG. 4 is a flow chart illustrating operation of the electromagnetic wave detection anti-blinding device.

As illustrated, the electromagnetic wave detection anti-blinding device includes an optical detecting unit 20, an electromagnetic wave detecting unit 30, a user interface 40, a main control unit 50 and a light transmission control unit 60.

The optical detecting unit 20 serves to detect light emitted from a welding or cutting torch, and includes a filter and an amplifier. Specifically, the optical detecting unit 20 compares output of a solar cell 3 with a signal input from the photo sensor 4 thus detecting a variation in the quantity of the light. The electromagnetic wave detecting unit 30 serves to detect electromagnetic waves emitted from the welding or cutting torch. Once an electromagnetic wave sensor 31 generates a signal in response to the electromagnetic waves emitted from the welding or cutting torch, the signal is subsequently subjected to resonance and filtering processes and then, the resonated and filtered signal is compared with a preset value, thus enabling detection of electromagnetic waves having a specific bandwidth. To this end, the electromagnetic wave detecting unit 30 includes a resonator to resonate the electromagnetic waves input through the electromagnetic wave sensor 31, and a filter to remove noise of an output of the resonator. In this case, the resonator and the filter are provided on a per coil basis. For example, when first and second coils are provided, pairs of resonators and filters are arranged parallel to each other.

The electromagnetic wave sensor 31 is configured to sense the electromagnetic waves emitted from the welding or cutting torch using at least two coils L1 and L2.

Preferably, the electromagnetic wave sensor 31 includes first and second bar-shaped coils L1 and L2 arranged in the form of a cross.

The user interface 40 includes a mode selector to select any one of the optical detecting unit 20 and the electromagnetic wave detecting unit 30 and a display member to display a selected mode.

The main control unit 50 is adapted to apply an electromagnetic wave detecting unit start-up signal to the electromagnetic wave detecting unit 30 and to monitor a variation of an electromagnetic wave signal received from an output of the electromagnetic wave detecting unit 30, when optical detection is started by the optical detecting unit 20.

The main control unit 50 is preferably a microcomputer or a control circuit including the microcomputer. According to an operational sequence determined by the main control unit 50, when the optical detection unit 20 starts optical detection and transmits an output thereof to the main control unit 50, the main control unit 50 applies an electromagnetic wave detecting unit start-up signal 33 to the electromagnetic wave detecting unit 30, so as to detect the electromagnetic waves input through the electromagnetic wave sensor 31. Thereby, the main control unit 50 monitors a variation in the quantity of light based on the output of the optical detection unit 20 and a variation of electromagnetic waves based on the output of the electromagnetic wave detecting unit 30. If no variation occurs, the operation is stopped until variation is again sensed.

The light transmission control unit 60 begins to operate when power supplied from the solar cell 3 reaches a predetermined value or more, thus serving to control light transmittance of the anti-blinding plate 5 based on an output signal of the main control unit 50.

FIG. 3 is a view illustrating the user interface of the electromagnetic wave detection anti-blinding device.

The electromagnetic wave detection anti-blinding device controls a variation in the light transmittance of the anti-blinding plate 5. The user interface 40 serves to adjust mode selection and mode display, light shade and light detection sensitivity, time delay and electromagnetic wave detection sensitivity. The electromagnetic wave sensor 31 senses the electromagnetic waves emitted from the welding or cutting torch using the at least two coils L1 and L2, and the first and second bar-shaped coils L1 and L2 are arranged in the form of a cross.

The electromagnetic wave sensor 31 may be attached to an upper portion of a welding helmet. Preferably, a plurality of electromagnetic wave sensors may be attached at two or more upper and lower positions of the welding helmet.

FIG. 4 is a flow chart illustrating operation of the above described anti-blinding device. Hereinafter, operation and effects of the electromagnetic wave detection anti-blinding device will be described with reference to FIG. 4.

First, the optical detecting unit 20 detects a variation in the quantity of light emitted from the welding or cutting torch (S1). If a detection signal from the optical detecting unit 20 is input into the main control unit 50 (S2), the main control unit 50 applies the electromagnetic wave detecting unit start-up signal 33 to the electromagnetic wave detecting unit 30 (S3). The electromagnetic wave detecting unit 30 compares en electromagnetic wave signal input from the electromagnetic wave sensor 31 with a preset reference value (S10 to S40). An integral type circuit including a resistor R8 and a condenser C5 of a time constant unit performs smoothing of a signal output from the electromagnetic wave detecting unit (S50). The smoothened signal is input into the main control unit 50 and is calculated by the microcomputer or the control circuit including the microcomputer so as to detect the quantity of electromagnetic waves (S60). The main control unit 50 changes a light transmittance of the anti-blinding plate 5 according to the calculated result from the main control unit 50. Accordingly, the main control unit 50 performs an operation to protect the welder's eyes more safely by detecting and controlling light and electromagnetic waves generated during a welding operation (S70).

The welding helmet having the above described configuration, however, has a problem in that the welder must take the welding helmet off to switch the anti-blinding device from a welding operation mode to a grinding operation mode or vice versa.

SUMMARY OF THE INVENTION

Therefore, the present invention has been made in view of the above problem, and it is an object of the present invention to provide a welding helmet including an anti-blinding device, which allows a welder to selectively switch the anti-blinding device from a welding operation mode to a grinding operation mode or vice versa by means of an external switch without taking off the welding helmet.

In accordance with an aspect of the present invention, the above and other objects can be accomplished by the provision of a welding helmet including an anti-blinding device to protect the welder's eyes from light emitted from a welding or cutting torch during a welding or grinding operation, wherein a switch is provided at an outer surface of the welding helmet to allow a welder to conveniently select an operation mode without taking off the welding helmet upon switching the anti-blinding device from a welding operation mode to a grinding operation mode or vice versa.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, exemplary embodiments of the present invention will be described in detail with reference to the accompanying drawings.

Referring to FIGS. 5 to 11, a welding helmet 100, which includes an anti-blinding device 110 to protect the welder's eyes from light emitted from a welding or cutting torch during a welding or grinding operation, has a feature in which a switch 150 is provided at an outer surface of the welding helmet 100 to allow a welder to rapidly and conveniently select a welding operation mode or a grinding operation mode of the anti-blinding device without taking off the welding helmet 100.

The anti-blinding device 110 is provided at a front surface of the welding helmet 100 and includes an anti-blinding plate 120 to shield welding light emitted from a welding or cutting torch so as to protect the welder's eyes operation during a welding or grinding operation.

When a welding operation is changed to a grinding operation or vice versa, conventionally, the welder must take the welding helmet off and switch the anti-blinding device from a welding operation mode to a grinding operation mode or vice versa. This makes it difficult for the welder to successively perform both the welding and grinding operations and causes difficulty in that the welding helmet must be taken off.

In the present invention, the switch 150 is provided at the outer surface of the welding helmet 100 at a lateral position to allow the welder to conveniently and directly switch the anti-blinding device 110 from the welding operation mode to the grinding operation mode or vice versa by manually operating the switch 150.

One exemplary embodiment of the present invention is as follows.

Figure 1:
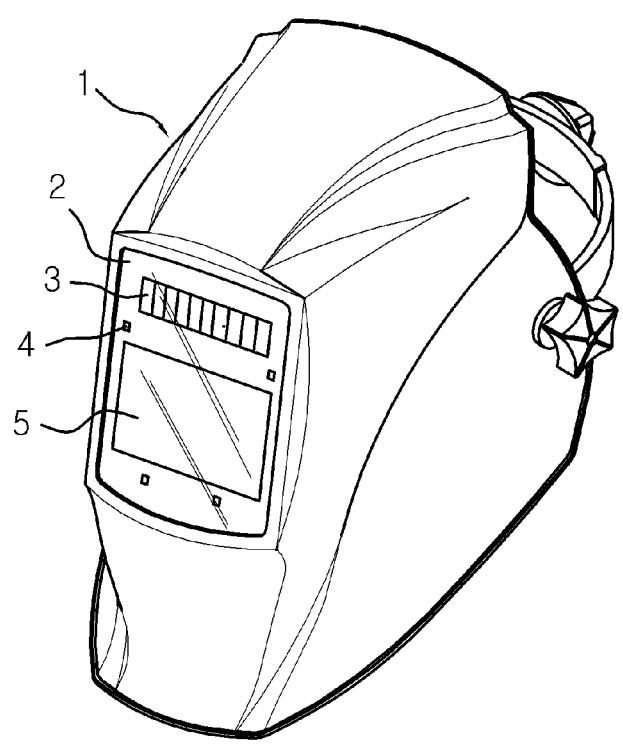
FIGS. 1 to 4 are views illustrating conventional anti-blinding devices.
Figure 2:
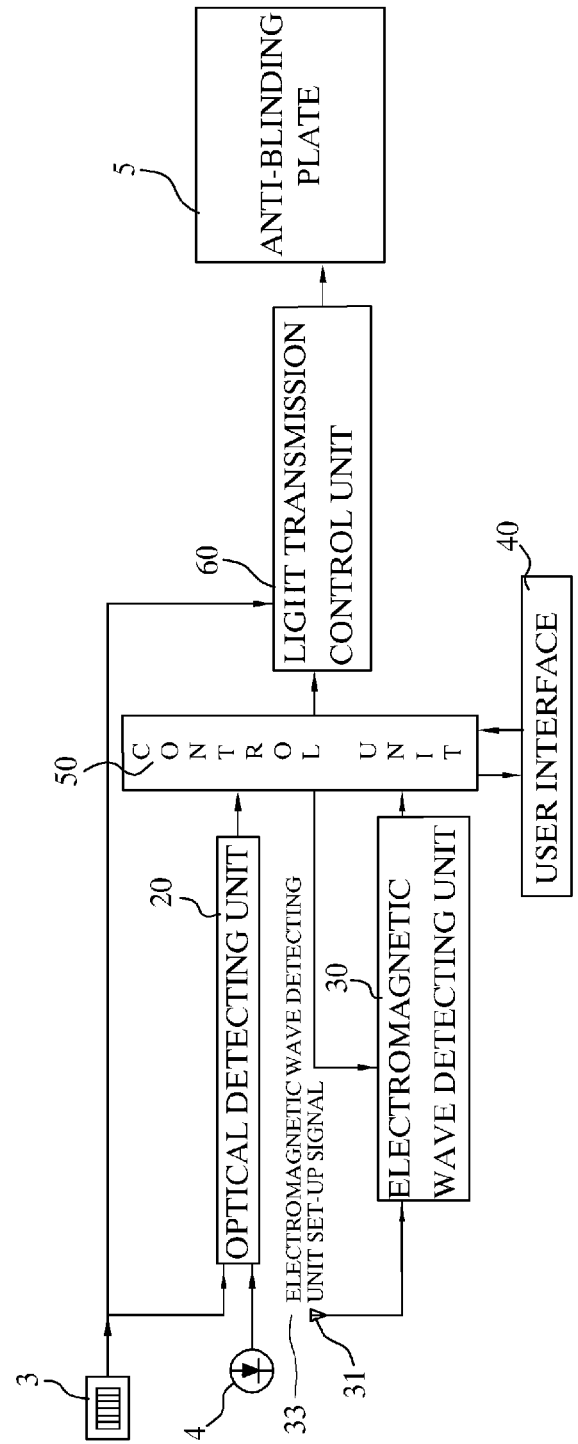
Figure 3:
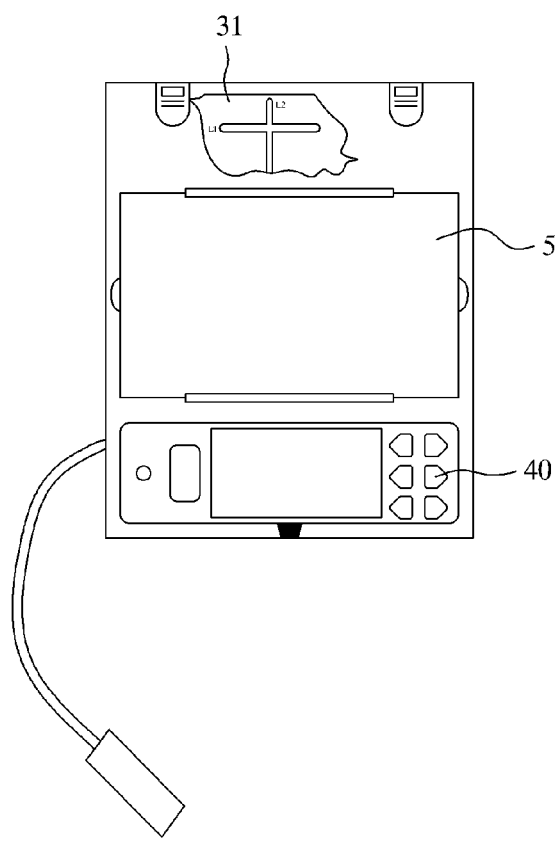
Figure 4:
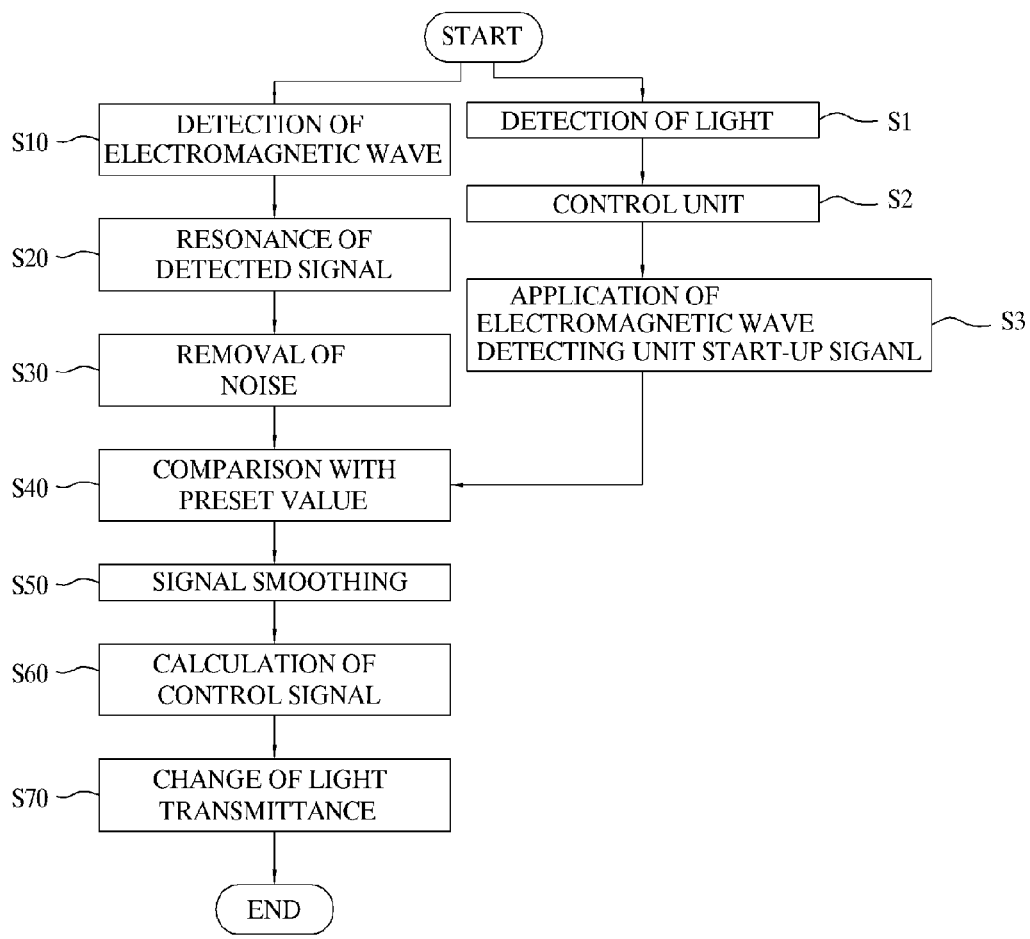
Figure 5:
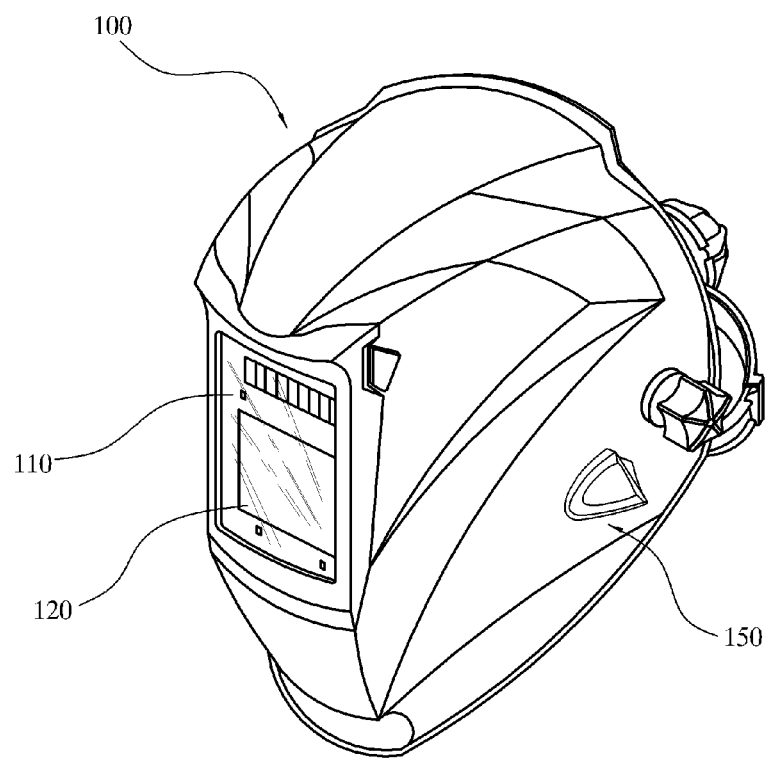
FIG. 5 is a perspective view illustrating a welding helmet including an anti-blinding device to selectively control a welding operation and a grinding operation according to one exemplary embodiment of the present invention.
Figure 6:
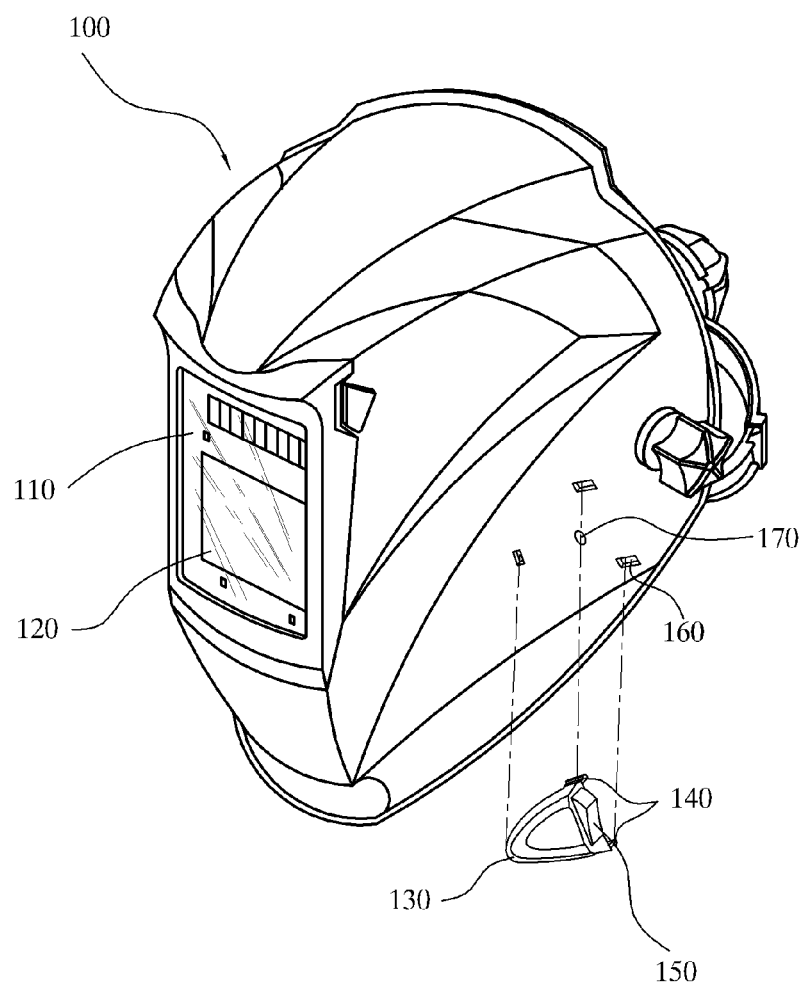
FIG. 6 is a perspective view illustrating a coupling relationship between the welding helmet and a switch illustrated in FIG. 5.
Figure 7:
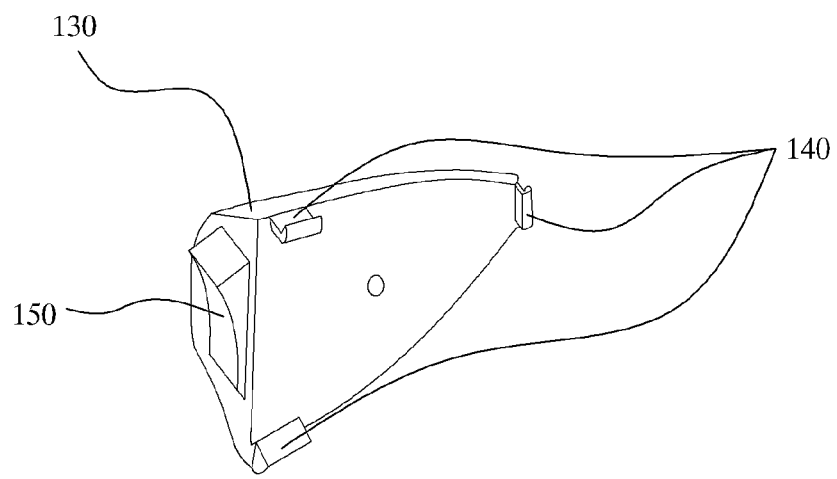
FIG. 7 is a perspective view of the switch illustrated in FIGS. 5 and 6.

As illustrated in FIGS. 6 and 7, to install the switch 150 to the welding helmet 100, the welding helmet 100 is formed with an electric line insertion hole 170, into which a communication cable 220 can be inserted, and fitting holes 160 arranged in a triangular form around the insertion hole 170. The switch 150 includes a case 130 provided at a lower surface thereof with fitting protrusions 140 to be separably fitted into the respective fitting holes 160.

Figure 8:
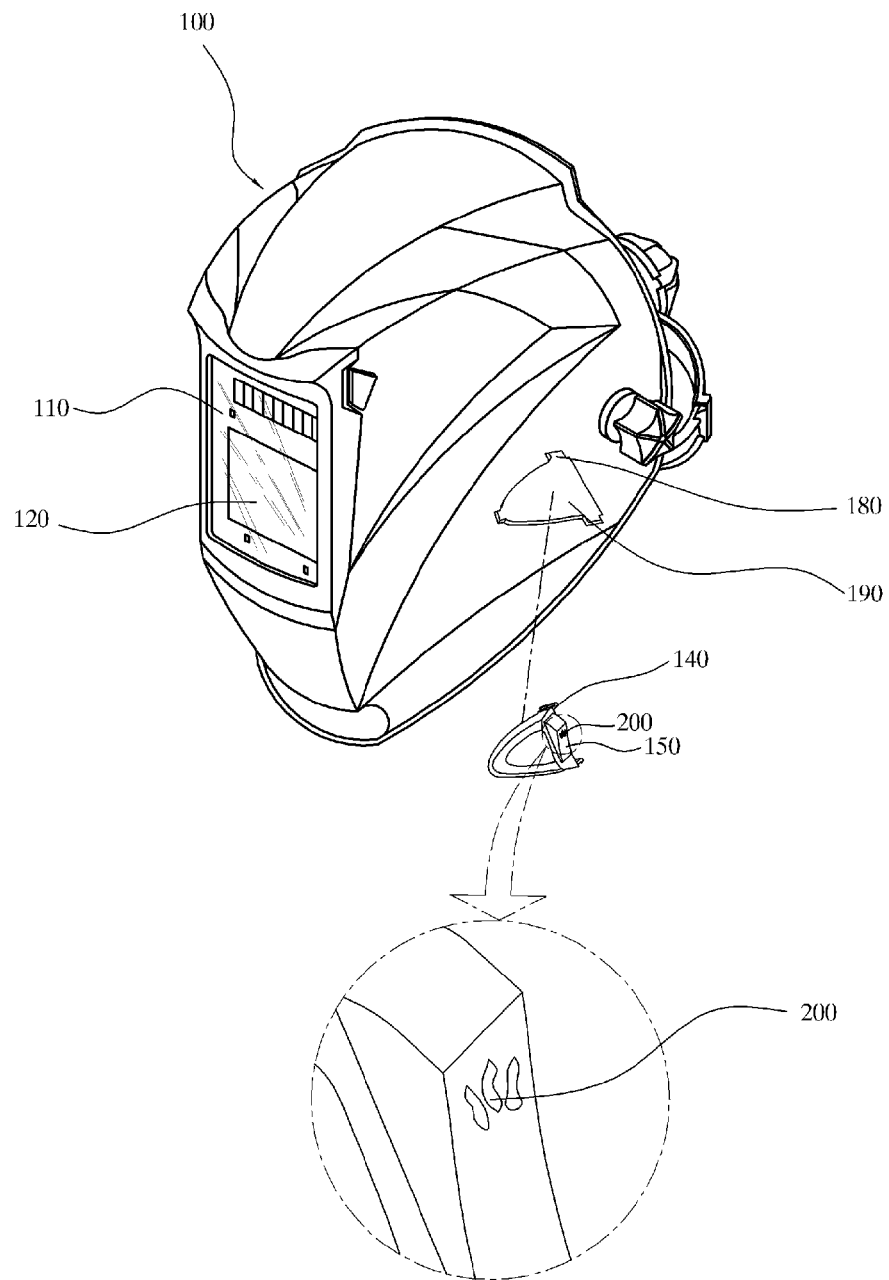
FIG. 8 is a perspective view illustrating a welding helmet including an anti-blinding device to selectively control a welding operation and a grinding operation according to another exemplary embodiment of the present invention.

FIG. 8 illustrates another exemplary embodiment of the present invention. As illustrated, the welding helmet 100, which includes the anti-blinding device to selectively control a welding operation and a grinding operation, is provided with the switch 150. To install the switch 150 to the welding helmet 100, in the present embodiment, the welding helmet 100 is formed with a triangular through-hole 190, and in turn, the triangular through-hole 190 is provided at three apexes thereof with fitting recesses 180 such that the fitting protrusions 140 are respectively fitted into the fitting recesses 180.

With the above described configuration using the through-hole 190 and the fitting recesses 180 formed at the apexes of the through-hole 190, a separate electric line insertion hole may be omitted.

In a state wherein the switch 150 is assembled through the fitting recesses 180 as described above, the welder can easily switch the anti-blinding device 100 from a welding operation mode to a grinding operation mode or vice versa while wearing the welding helmet 100.

The switch 150 may be provided with a mark protrusion 200 to sense finger touch when the welder manually operates the switch 150 to switch the anti-blinding device 110 from the welding operation mode to the grinding operation mode or vice versa.

Figure 9:
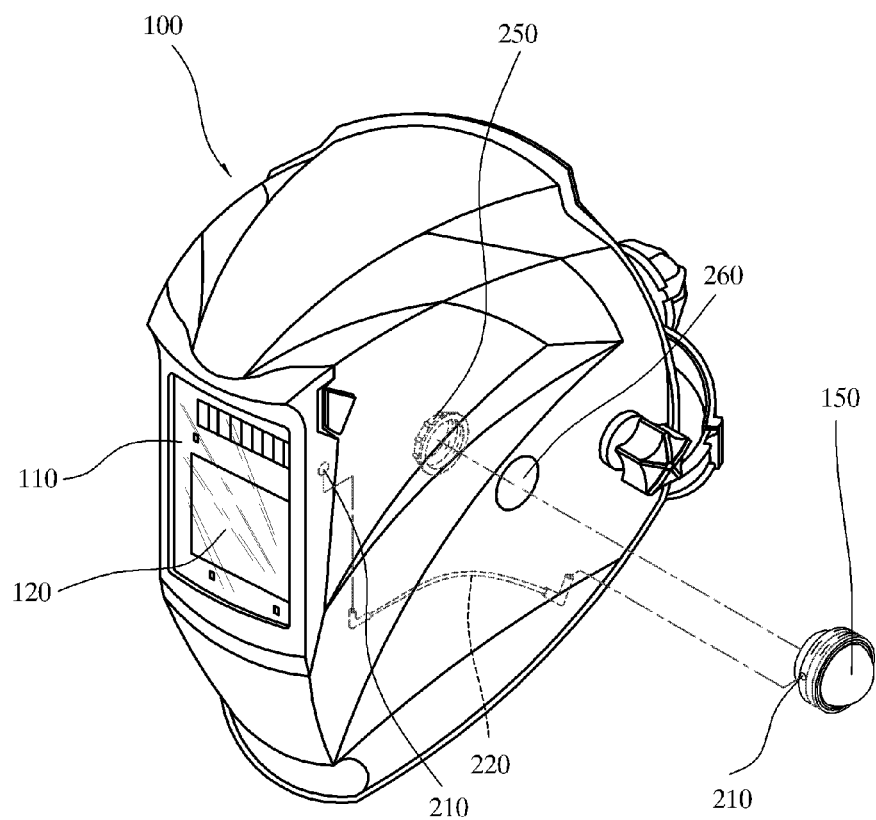
FIG. 9 is a perspective view illustrating a welding helmet including an anti-blinding device to selectively control a welding operation and a grinding operation according to another exemplary embodiment of the present invention.
Figure 10:
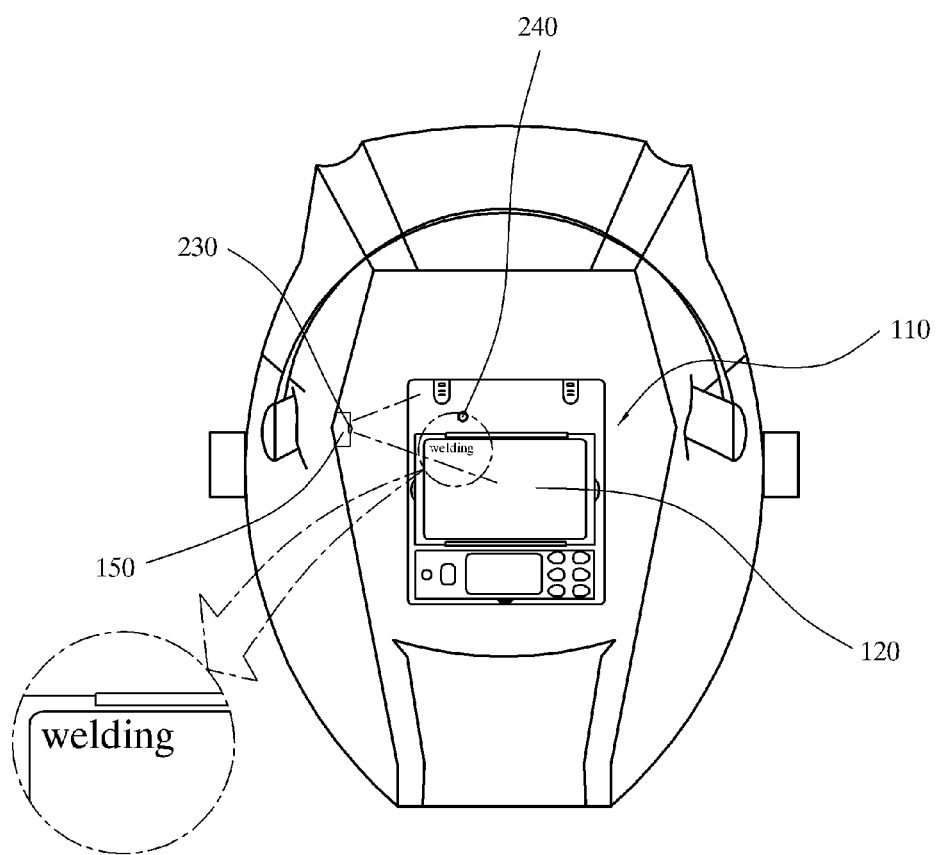
FIG. 10 is a front view illustrating a welding operation mode according to the present invention.
Figure 11:
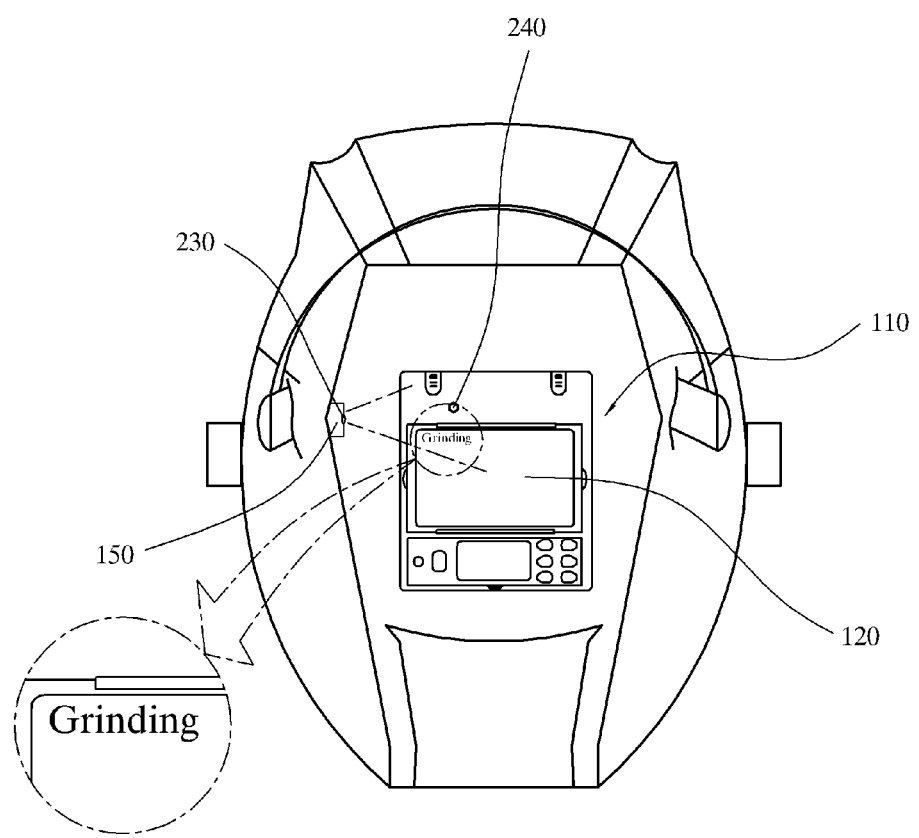
FIG. 11 is a view illustrating a grinding operation mode according to the present invention.

FIGS. 9 to 11 illustrate the welding helmet 100 including the anti-blinding device 110 configured to be conveniently and easily controlled by means of the switch 150 according to another exemplary embodiment of the present invention.

In the present embodiment, the switch 150 is provided with an infrared sending unit 230 including a battery, and the anti-blinding device 100 is provided with an infrared receiving unit 240. The infrared sending and receiving units 230 and 240 may be controlled in a wireless manner, or the communication cable 220 may be connected to connection jacks 210 provided respectively at the switch 150 and the anti-blinding device 100 to enable wired control upon discharge of the battery of the switch 150.

As described above, the switch 150 and the anti-blinding device 110 may perform sending and receiving of signals by use of infrared rays in a wireless manner.

In an alternative embodiment, i.e. when the battery (not shown) is discharged, as illustrated in FIG. 9, the connection jacks 210 may be provided respectively at the switch 150 and the anti-blinding device 110 and may be connected to each other via the communication cable 220, such that the switch 150 and the anti-blinding device 110 are controlled in a wired manner. That is, the switch 150 and the anti-blinding device 100 may simultaneously adopt both wired and wireless control manners.

In the embodiment as illustrated in FIG. 9, the welding helmet 100 is formed with a coupling hole 260. After the switch 150 is fitted into the coupling hole 260, a fastening nut 260 is fastened around the switch 150 to fix a position of the switch 150.

The above described configuration enables compatible use of the communication cable 220 such that the communication cable 220 may be removed when not in use.

FIGS. 10 and 11 illustrate the anti-blinding plate 120, which functions to display whether the welding helmet 100 is in a welding operation mode or in a grinding operation mode. Specifically, a Liquid Crystal Display (LCD) of the anti-blinding plate 120 informs of a current status by displaying words "Welding" and "Grinding".

Accordingly, the present invention eliminates troublesome use of a conventional anti-blinding device usable with a welding helmet that requires the welder to take the welding helmet off whenever it is necessary to switch the anti-blinding device from a welding operation mode to a grinding operation mode or vice versa.

Figure 12:
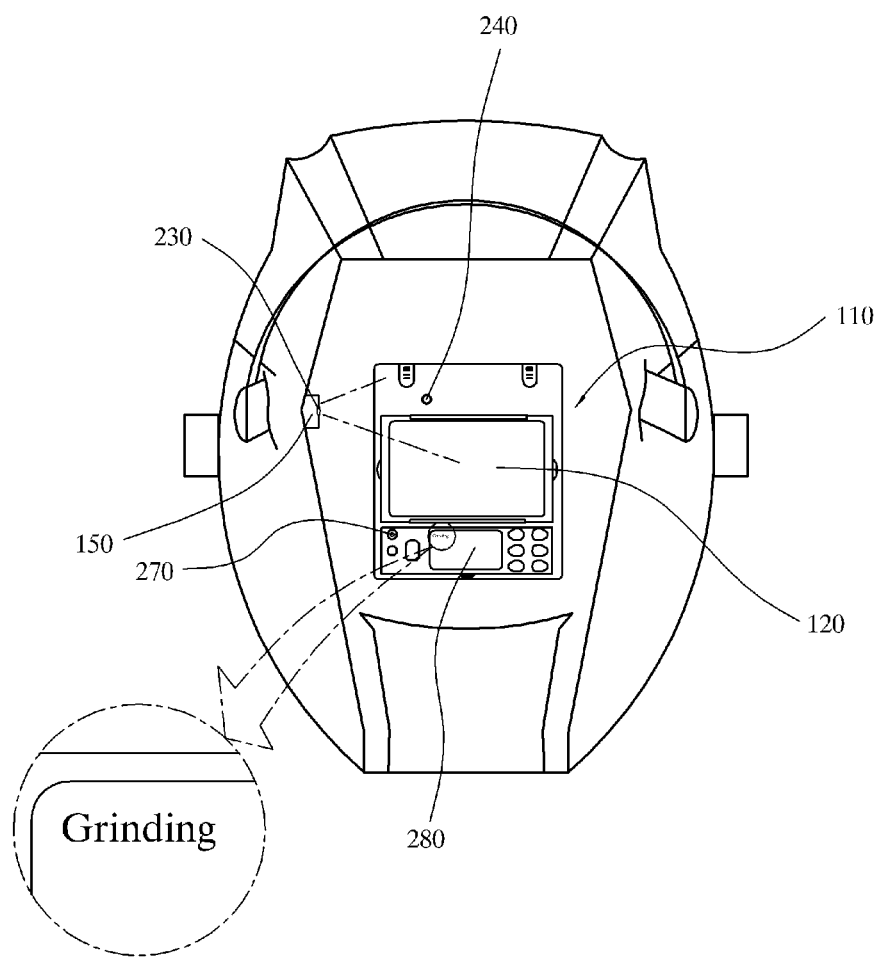
FIG. 12 is a view illustrating a Light Emitting Diode (LED) lamp and control panel for display of an operation mode according to a further exemplary embodiment of the present invention.

Referring to FIG. 12, a Light Emitting Diode (LED) lamp 270 may be embedded in the welding helmet so as to be turned on during a grinding operation, thus allowing the welder to easily recognize whether or not a current operation mode is a grinding operation mode.

In addition, the anti-blinding device may be provided with a control panel 280 to display a current status using words "Welding" and "Grinding".

In an alternative embodiment of the present invention, the switch may be provided with a touch sensor. In this case, the welder may switch the anti-blinding device from a welding operation mode to a grinding operation mode or vice versa by simply touching the switch once.

As apparent from the above description, the present invention provides a welding helmet including an anti-blinding device, which can allow the welder to successively perform a welding operation and a grinding operation without taking off the welding helmet by means of a switch that directly switches the anti-blinding device from a welding operation mode to a grinding operation mode or vice versa.

Accordingly, the present invention is very useful in the viewpoint that the welder can rapidly and effectively perform the welding operation and the grinding operation in succession.

The above description related to the preferred embodiments of the present invention and the accompanying drawings have been provided for illustrative purposes, and are not intended to limit the scope of the present invention defined by the claims. Thus, those skilled in the art will appreciate that various modifications, additions and substitutions are possible, without departing from the scope and spirit of the invention as disclosed in the accompanying claims. Accordingly, the technical protection range of the present invention should be determined by the appended claims.

What is claimed is:

1. A welding helmet including an anti-blinding device to selectively and conveniently control a welding operation and a grinding operation, the anti-blinding device serving to protect welder's eyes from light emitted from a welding or cutting torch during the welding or grinding operation,
    wherein a switch is provided at an outer surface of the welding helmet, the switch being turned on or turned off to switch the anti-blinding device from a welding operation mode to a grinding operation mode or vice versa,
    wherein the switch includes a case provided at a bottom surface thereof with a fitting protrusion and the welding helmet is formed at a lateral position thereof with an electric line insertion hole and a fitting hole, whereby the fitting protrusion of the switch is fitted into the fitting hole to couple the switch to the welding helmet,
    wherein the switch comprises a curved surface to allow the welder to operate the switch by sliding a finger over the switch, and the switch further comprises a plurality of mark protrusions formed on the curved surface to allow the welder to easily locate the switch, wherein the switch is configured to hide the curved surface when the welding helmet is viewed from a front of the helmet, wherein the switch is configured to rapidly switch the anti-blinding device from the welding operation mode to the grinding operation mode or vice versa, wherein the anti-blinding device includes a liquid crystal display or a control panel to indicate a current status thereof by displaying words "Welding" and "Grinding," and wherein a Light Emitting Diode (LED) lamp is embedded in the welding helmet so as to be turned on during a grinding operation for easy recognition of a current status.

* * * * *